United States Patent
Reyneke et al.

(10) Patent No.: US 11,117,108 B2
(45) Date of Patent: Sep. 14, 2021

(54) USE OF A FUEL OIL WASH TO REMOVE CATALYST FROM A FLUIDIZED-BED PROPANE DEHYDROGENATION REACTOR EFFLUENT

(71) Applicants: Rian Reyneke, Katy, TX (US); Jose Manuel Urquiaga, Houston, TX (US); Truc Vu, Houston, TX (US); Jeffrey Donald Caton, Missouri City, TX (US)

(72) Inventors: Rian Reyneke, Katy, TX (US); Jose Manuel Urquiaga, Houston, TX (US); Truc Vu, Houston, TX (US); Jeffrey Donald Caton, Missouri City, TX (US)

(73) Assignee: Kellogg Brown & Root LLC, Houston, TX (US)

( * ) Notice: Subject to any disclaimer, the term of this patent is extended or adjusted under 35 U.S.C. 154(b) by 0 days.

(21) Appl. No.: 16/570,029

(22) Filed: Sep. 13, 2019

(65) Prior Publication Data
US 2021/0077967 A1 Mar. 18, 2021

(51) Int. Cl.
| | | |
|---|---|---|
| *B01J 8/00* | (2006.01) | |
| *B01J 8/02* | (2006.01) | |
| *B01J 8/18* | (2006.01) | |
| *B01J 39/12* | (2006.01) | |

(Continued)

(52) U.S. Cl.
CPC ........... *B01J 8/006* (2013.01); *B01J 8/0015* (2013.01); *B01J 8/0278* (2013.01); *B01J 8/1836* (2013.01); *B01J 38/12* (2013.01); *C07C 5/3332* (2013.01); *B01J 2208/00761* (2013.01); *B01J 2208/00787* (2013.01); *B01J 2208/00991* (2013.01)

(58) Field of Classification Search
CPC ... B01J 8/00; B01J 8/0015; B01J 8/005; B01J 8/006; B01J 8/02; B01J 8/0278; B01J 8/18; B01J 8/1836; B01J 38/00; B01J 38/04; B01J 38/12; B01J 2208/00; B01J 38/0743; B01J 38/00761; B01J 38/00769; B01J 38/00787; B01J 38/00796; B01J 38/00991; C07C 5/00; C07C 5/32; C07C 5/327; C07C 5/333; C07C 5/3332
See application file for complete search history.

(56) References Cited

U.S. PATENT DOCUMENTS

| | | | |
|---|---|---|---|
| 7,011,740 B2 * | 3/2006 | Tallman | C10G 11/18 208/113 |
| 7,935,650 B2 | 5/2011 | Corradi et al. | |
| 9,834,496 B2 | 12/2017 | Pretz et al. | |

(Continued)

FOREIGN PATENT DOCUMENTS

WO    WO-2018037330 A1 *    3/2018    ............. C07C 5/333

OTHER PUBLICATIONS

International Search Report and Written Opinion dated Dec. 10, 2020 for International Application No. PCT/US2020/050052; International filed Sep. 10, 2020; 16 pages.

*Primary Examiner* — Natasha E Young
(74) *Attorney, Agent, or Firm* — Gary M. Machetta

(57) ABSTRACT

A process where external fuel oil is used to wash entrained catalyst from a fluidized-bed propane dehydrogenation reactor effluent, where the fuel oil and catalyst mixture is returned to the reactor to provide the net fuel required for catalyst regeneration. Optionally the fluidized-bed propane dehydrogenation reactor effluent and the fuel oil are contacted in a direct contact inline device before entering a flash zone in the reactor vessel.

17 Claims, 2 Drawing Sheets

A Quench Tower
B Oil Wash Section
C Filter
D Filtered Oil Heat Exchanger

1 Reactor Effluent (Vapor)
2 External Wash (Liquid, Fuel Oil)
3 Oil-Catalyst Slurry (Liquid)
4 Filtered Wash Oil Filtration Loop (Liquid)
5 Recovered Catalyst (Liquid)
6 Cooled Effluent Gas (Vapor)

(51) Int. Cl.
*C07C 5/333* (2006.01)
*B01J 38/12* (2006.01)

(56) References Cited

U.S. PATENT DOCUMENTS

| | | |
|---|---|---|
| 2005/0204281 A1 | 10/2005 | Bjorklund et al. |
| 2009/0325783 A1 | 12/2009 | Myers et al. |
| 2012/0108877 A1 | 5/2012 | Myers |
| 2020/0299212 A1 | 9/2020 | Tallman et al. |

\* cited by examiner

USE OF A FUEL OIL WASH TO REMOVE CATALYST FROM A FLUIDIZED-BED PROPANE DEHYDROGENATION REACTOR EFFLUENT

TECHNICAL FIELD

The present invention relates to a process for removing catalyst from an effluent, and more particularly relates to a process for removing catalyst from a Propane Dehydrogenation (PDH) reactor effluent stream using a wash fluid and filtration.

BACKGROUND

The abundance of alkanes and paraffins from shale and stranded gas has spurred the development of more cost-effective ways to produce light olefins, the demand for which has increased significantly in recent years. Steam cracker units have been designed to use lighter shale condensates as feedstock to meet the increase in the demand for light olefins, like ethylene. However, these units have been found to be deficient for propylene production due to the low propylene/ethylene ratio and low propylene yield. As a result, finding routes for the targeted production of propylene have received considerable interest.

It has been shown that catalytic dehydrogenation provides the possibility of high selectivity to a single olefin product. Current alkane dehydrogenation processes for the production of propylene and other light olefins employ the use of platinum-based and chromium-based catalysts. Given the expense associated with platinum and the carcinogenic properties of chromium, there is a need for developing less expensive, less toxic metal oxide catalysts that are capable of good alkene selectivity during the dehydrogenation process and a correspondingly high yield.

A potential deficiency in processes for alkane or paraffin dehydrogenation employing a riser or fluidized-bed type reactor is the amount of catalyst particles including fines in the effluent streams leaving the dehydrogenation reactor. With regard to the reactor effluent stream, a water quench tower is used to cool the reactor effluent and condense the water therein, particularly if dilution steam is used to lower the partial pressure of the alkane or paraffin. The catalyst and fines contained in the reactor effluent stream cannot easily be separated from quench water, leading to excessive fouling in the equipment and consequential high maintenance costs. Thus, there is also a need for improved recovery of catalyst fines found in the effluent stream from the dehydrogenation reactor.

Some catalyst is entrained from the reactor and needs to be removed before entering downstream separation steps. The reactor effluent contains steam (water) from either dilution steam or stripping/fluidizing steam added in the reactor. After cooling the reactor effluent and condensing out the water in the effluent, separation of catalyst from water is problematic since the mixture becomes mud-like, which is difficult to filter or transport. Even if the catalyst is filtered, the resulting water-catalyst slurry is not suitable to be returned to the reactor for catalyst recovery.

SUMMARY

Figure 1:
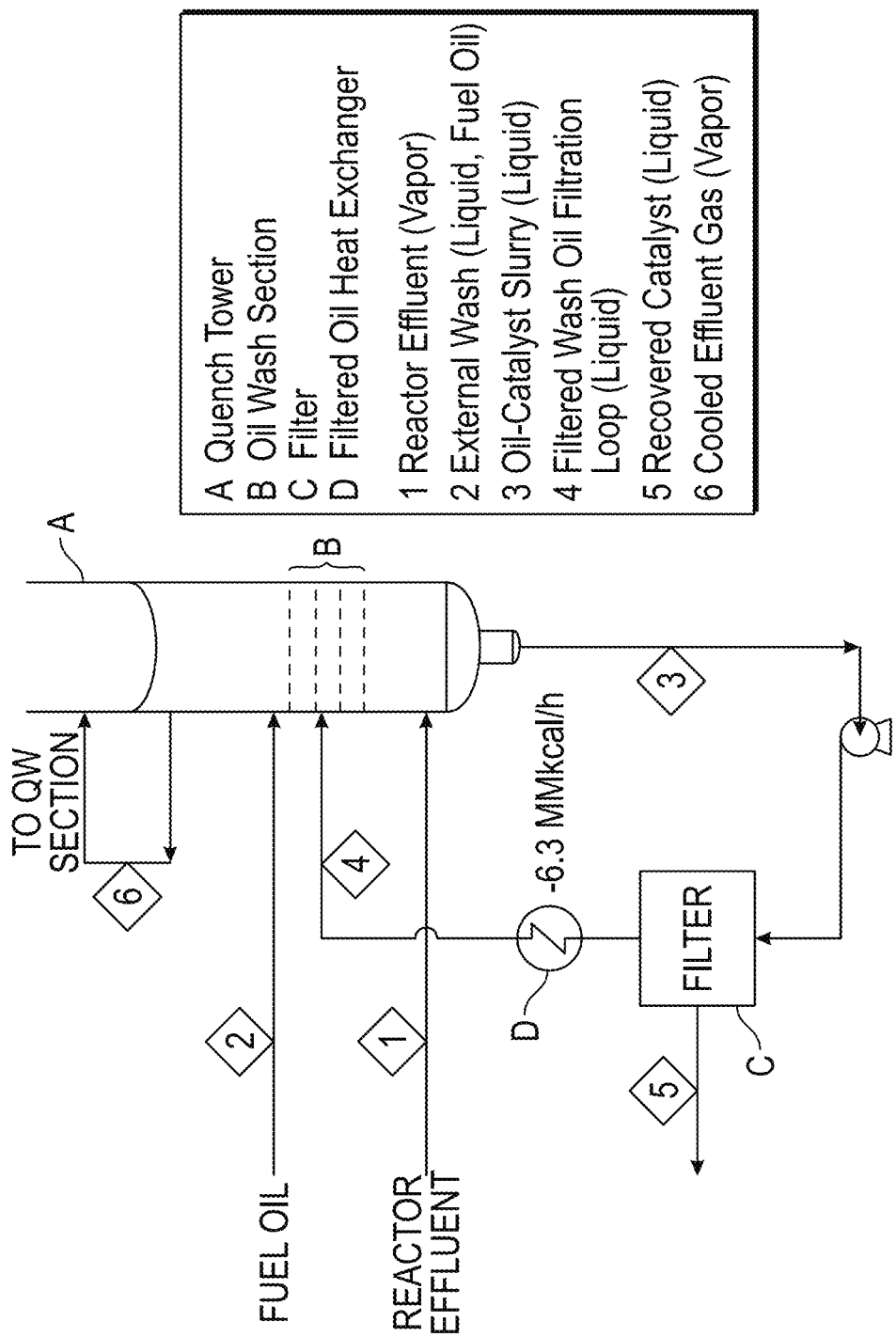
FIG. 1 is a non-limiting, schematic illustration of a process for using a fuel oil wash to remove catalyst from a fluidized-bed propane dehydrogenation reactor effluent described herein.

There is provided, in one non-limiting embodiment a method for recovering catalyst from a fluidized-bed propane dehydrogenation reactor effluent gas, where the method includes (a) cooling fluidized-bed propane dehydrogenation reactor effluent gas, (b) contacting the effluent gas with fuel oil in a wash section to wash out catalyst to obtain a cooled effluent gas essentially free of catalyst, (c) withdrawing an oil-catalyst slurry from the wash section and circulating the oil-catalyst slurry through a filter thereby removing catalyst from the fuel oil giving filtered wash oil, (d) returning filtered wash oil to the wash section as recirculated wash oil; and (e) backwashing the filter thereby recovering catalyst. Optionally the method further includes contacting the effluent gas with fuel oil in a direct contact inline device prior to entering a flash zone, followed by removing a net amount of fuel oil and a majority of the catalyst as a concentrated bottom oil-catalyst slurry.

There is further provided in another non-restrictive version a system for recovering catalyst from a fluidized-bed propane dehydrogenation reactor effluent gas, where the system includes a quench tower having an inlet for receiving the effluent gas, vapor-liquid contacting elements disposed above the inlet for cooling the effluent gas and washing out the catalyst, a gas outlet above the contacting elements for discharging cooled effluent gas essentially free of catalyst, and a liquid holdup zone below the inlet for collecting the fuel oil from the contacting elements, at least one filter operable in filtration and backwashing modes, and a filtration loop for circulating fuel oil from the liquid holdup zone through a filter and returning filtrate to the liquid holdup zone. Optionally the system further includes a direct contact inline device that receives and mixes the fluidized-bed propane dehydrogenation reactor effluent and the fuel oil prior to injecting them into a flash zone.

DETAILED DESCRIPTION

It has been discovered that contacting one or more metal oxide catalysts with a paraffin having 2-8 carbon atoms in a dehydrogenation reaction for a period ranging from about 0.05 seconds to about 10 minutes in a reactor, in a non-limiting embodiment, may lead to better selectivity for certain olefins, such as propylene and butylene. It has also been discovered that metal oxide catalyst particles and fines, generated because of attrition in a riser or fluidized-bed type reactor, are contained within the reactor effluent stream. These catalyst particles and fines may be recovered by contacting the effluent stream of the reactor with a wash fluid, in one non-limiting embodiment external fuel oil, to form a cooled catalyst effluent stream and a substantially catalyst-free product stream and then filtering the cooled catalyst effluent stream with one or more filters to capture the catalyst fines for potential reuse. As used herein in one non-limiting embodiment "essentially free of catalyst" is defined as having no problematic amounts of catalyst particles or fines, or catalyst is removed up to the practical limits.

In one embodiment, the paraffin to be contacted with the metal oxide catalyst(s) may include, but not necessarily be limited to, propane, ethane, n-butane, isobutane, and combinations thereof. In another embodiment, the paraffin may be introduced to the reactor with or without an inert diluent or steam.

The metal oxide catalysts useful in dehydrogenating the paraffin to produce a light olefin product gas may be made up of one or more of the following oxides: zinc, titanium, copper, iron, manganese, aluminum, silicon, zirconium, cerium, dysprosium, erbium, europium, gadolinium, lanthanum, neodymium, praseodymium, samarium, terbium, ytterbium, yttrium, or niobium. In a non-limiting embodiment, the metal oxide catalyst(s) used are substantially free of platinum and chromium.

The dehydrogenation of the paraffin using metal oxide catalysts of the kinds described above and recovery of catalyst fines in the reactor effluent stream may be accomplished, in one non-limiting embodiment, by a process in which a paraffin feedstock comprising paraffins having 2-8 carbons is contacted with one or more metal oxide catalysts in a riser or fluidized bed reactor under dehydrogenation conditions. This process may be performed at a reaction temperature of about 500-800° C., a space velocity of about 0.1-1 $h^{-1}$, and a pressure of about 0.01-0.2 MPa. In one non-restrictive version, the reaction period may range from about 0.05 seconds to about 10 minutes. In other non-limiting embodiments, the dehydrogenation reaction between the paraffin and the metal oxide catalyst(s) may also be carried out in a fixed-bed swing or riser or fluidized-bed reactor from which a reactor effluent stream is formed.

As schematically illustrated in FIG. 1, in one non-restrictive version, effluent from a fluidized bed propane dehydrogenation reactor 1 contains small amounts of entrained catalyst, which may be understood to be catalyst particles and/or fines, such as metal oxide catalysts and/or fines previously discussed. After cooling the effluent 1 against reactor feed 1, the gas 1 is contacted with a circulating oil in a quench tower A or other vessel, in a non-limiting embodiment, an external fuel oil 2 to wash out any entrained catalyst, and carry it back to the reactor regenerator to recover the catalyst and provide fuel for regeneration. The washing step occurs in an oil wash section B of quench tower A, which oil wash section B utilizes a contact device such as trays or packing to ensure good contact between the wash oil 2 and the process effluent gas 1, for effective removal of the catalyst. Wash oil 2 from an external sources is added to the top of this wash section B. An oil-catalyst slurry 3 is withdrawn from the bottom of the wash section B and at least part of the flow is circulated through a filtration system or filter C that removes catalyst from the oil-catalyst slurry 3. Filtered wash oil 4 is cooled (heat is used for process heating) in filtered oil heat exchanger D and returned to the top of the wash section B. When the filter(s) C is backwashed, recovered catalyst 5 along with the net amount of wash oil that was added to the system is routed to the reactor system regenerator, where the wash oil provides the net heat required for catalyst regeneration. Cooled effluent gas 6 is recirculated to the quench water (QW) section.

The oil wash section B could be a separate column or in one non-limiting embodiment be integrated as a lower section of a water quench tower A, as shown in FIG. 1.

One option for the catalyst filtration device C would be to use a multi-bed system with fixed filtration medium such as a sintered metal-type filter. After the filtration bed is loaded with catalyst, the circulating oil flow 3 would be switched to a second filter, while the first would be regenerated to clean the filter and recover the catalyst.

An alternative filtration device(s) C would be to use a continuous filtration system where oil flows through a drum-type filter, and catalyst is continuously removed from the inside surface of the filter and the concentrated catalyst-oil slurry is continuously removed and routed to the reactor regenerator.

Figure 2:
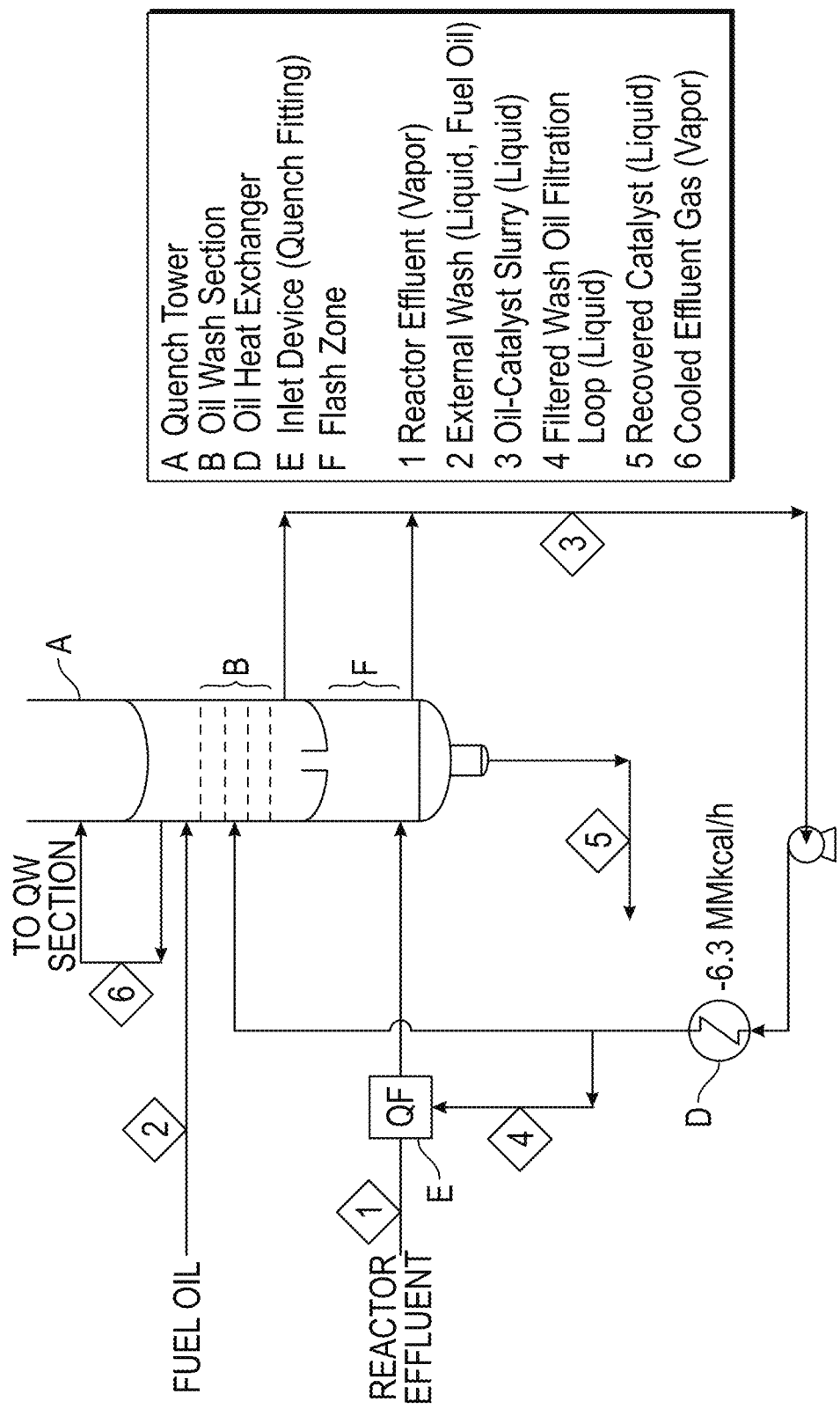
FIG. 2 is schematic illustration of another non-limiting embodiment a process for using a fuel oil wash to remove catalyst from a fluidized-bed propane dehydrogenation reactor effluent employing a flash zone described herein.

Alternatively, as schematically shown in FIG. 2, after cooling the fluidized-bed propane dehydrogenation reactor effluent gas 1 against reactor feed 1, the effluent gas 1 is contacted with fuel oil 4 in a direct contact inline device E (such as a quench fitting) before entering a flash zone F in a vessel A. In the flash zone F, a net amount of oil 2 and the majority of entrained catalyst is removed as a concentrated bottom catalyst-oil slurry 5 which can be directed to the reactor regeneration system (not shown) for catalyst recovery and to provide the net fuel requirements.

The gas from the flash zone F (which is nearly free of catalyst) next enters a wash section B that utilizes a contact device such as trays or packing to ensure good contact between the wash oil and the process gas, for effective removal of the remaining catalyst, as previously described. The oil 3 from the wash section B is pumped around and cooled (heat is used for process heating) in the oil heat exchanger D and returned to the top of the wash section B. A portion of this oil 4 is used in the direct contact inline device E as described above.

The flash zone and oil wash section together could be accommodated in a separate column or be integrated as a lower section of a water quench tower as schematically illustrated in FIG. 2.

Using the fuel oil intended for reactor regeneration as a wash oil 2 to remove catalyst from the reactor effluent 1 provides the technical and commercial advantages of an effective way to remove the catalyst, recovery of process heat and return recovered catalyst back to the reactor system. Application of the flash zone F design could eliminate the need for catalyst filters, or substantially reduce the size of filters, and also substantially reduce the catalyst content in the circulating fuel oil 3 used in the oil wash section B, which reduces the potential for fouling in this circuit.

In the foregoing specification, the invention has been described with reference to specific embodiments thereof. However, the specification is to be regarded in an illustrative rather than a restrictive sense. For example, paraffins, metal oxide catalysts, dehydrogenation reaction conditions and equipment, fuel oils, fluidized-bed propane dehydrogenation reactor effluents, catalyst fine recovery conditions and equipment falling within the claimed or disclosed parameters, but not specifically identified or tried in a particular example, are expected to be within the scope of this invention.

The present invention may be practiced in the absence of an element not disclosed. In addition, the present invention may suitably comprise, consist or consist essentially of the elements disclosed. For instance, there may be provided a method for recovering catalyst from a fluidized-bed propane dehydrogenation reactor effluent gas, where the method consists essentially of or consists of (a) cooling fluidized-bed propane dehydrogenation reactor effluent gas, (b) contacting the effluent gas with fuel oil in a wash section to wash out catalyst to obtain a cooled effluent gas essentially free of catalyst, (c) withdrawing an oil-catalyst slurry from the wash section and circulating the oil-catalyst slurry through a filter thereby removing catalyst from the fuel oil giving filtered wash oil, (d) returning filtered wash oil to the wash section as recirculated wash oil; and (e) backwashing the filter thereby recovering catalyst. Optionally the method further consists essentially of or consists of contacting the effluent gas with fuel oil occurs in a direct contact inline device prior to entering a flash zone, followed by removing a net amount of fuel oil and a majority of the catalyst as a concentrated bottom oil-catalyst slurry.

Alternatively, there may be provided in another nonrestrictive version a system for recovering catalyst from a fluidized-bed propane dehydrogenation reactor effluent gas, where the system consists essentially of or consists of a quench tower having an inlet for receiving the effluent gas, vapor-liquid contacting elements disposed above the inlet for cooling the effluent gas and washing out the catalyst, a gas outlet above the contacting elements for discharging cooled effluent gas essentially free of catalyst, and a liquid holdup zone below the inlet for collecting the fuel oil from the contacting elements, at least one filter operable in filtration and backwashing modes, and a filtration loop for circulating fuel oil from the liquid holdup zone through a filter and returning filtrate to the liquid holdup zone. Optionally the system further consists essentially of or consists of a direct contact inline device that receives and mixes the fluidized-bed propane dehydrogenation reactor effluent and the fuel oil prior to injecting them into a flash zone.

The words "comprising" and "comprises" as used throughout the claims, are to be interpreted to mean "including but not limited to" and "includes but not limited to", respectively.

As used herein, the word "substantially" shall mean "being largely but not wholly that which is specified."

As used herein, the singular forms "a," "an," and "the" are intended to include the plural forms as well, unless the context clearly indicates otherwise.

As used herein, the term "about" in reference to a given parameter is inclusive of the stated value and has the meaning dictated by the context (e.g., it includes the degree of error associated with measurement of the given parameter).

As used herein, the term "and/or" includes any and all combinations of one or more of the associated listed items.

The invention claimed is:

1. A method for recovering catalyst from a fluidized-bed propane dehydrogenation reactor effluent gas, the method comprising:
    (a) cooling fluidized-bed propane dehydrogenation reactor effluent gas;
    (b) contacting the cooled effluent gas with fuel oil in a wash section to wash out catalyst to obtain a cooled effluent gas essentially free of catalyst;
    (c) withdrawing an oil-catalyst slurry from the wash section and circulating the oil-catalyst slurry through a filter thereby removing catalyst from the fuel oil giving filtered wash oil;
    (d) returning filtered wash oil to the wash section as recirculated wash oil; and
    (e) backwashing the filter thereby recovering catalyst.

2. The method of claim 1 wherein the contacting and returning steps are effected in a quench tower comprising vapor-liquid contact elements and a bottoms zone holding a fuel oil inventory.

3. The method of claim 1 further comprising cooling the recirculated wash oil before the contacting step.

4. The method of claim 1 wherein circulating the oil-catalyst slurry through a filter comprises continuously passing the oil-catalyst slurry through at least one first filter in a filtration mode to separate the catalyst therefrom giving filtrate while at least one second filter in parallel with the first filter is in a backwashing mode thereby removing the separated catalyst therefrom.

5. The method of claim 4 further comprising returning filtrate from the first filter to the fuel oil inventory.

6. The method of claim 4 wherein the backwashing of the at least one filter further comprises periodically alternating the at least one first and the at least one second filters between the filtration and backwashing modes.

7. The method of claim 4 wherein the backwashing includes at least once pulsing compressed gas through the second filter for catalyst removal.

8. The method of claim 2 wherein the fuel oil is a portion of the fuel oil from the fuel oil inventory.

9. The method of claim 1 wherein the filter is a multi-bed system comprising multiple beds each bed comprising a fixed filtration medium, where in the method the circulating the oil-catalyst slurry through the multi-bed system further comprises:
    (a) circulating the oil-catalyst slurry through at least a first bed thereby loading the first bed with catalyst,
    (b) switching circulating the oil-catalyst slurry through at least a second bed while regenerating the at least first bed and recovering the catalyst.

10. The method of claim 9 wherein the fixed filtration medium is a sintered metal filter.

11. The method of claim 1 wherein the filter is a continuous filtration system comprising a drum filter having an inside surface, where in the method the circulating the oil-catalyst slurry through the continuous filtration system comprises:
    (a) continuously removing catalyst from the inside surface; and
    (b) continuously removing concentrated oil-catalyst slurry and routing it to a reactor generator.

12. The method of claim 1 wherein in the method contacting the effluent gas with fuel oil occurs in a direct contact inline device prior to entering a flash zone, followed by removing a net amount of fuel oil and a majority of the catalyst as a concentrated bottom oil-catalyst slurry.

13. The method of claim 1 further comprising introducing at least a portion of the slurry from the circulating step into a catalyst regenerator for combustion to regenerate and heat the catalyst.

14. A system for recovering catalyst from a fluidized-bed propane dehydrogenation reactor effluent gas, the system comprising:
    (a) a quench tower having an inlet for receiving the effluent gas, vapor-liquid contacting elements disposed above the inlet for cooling the effluent gas and washing out the catalyst;
    (b) a gas outlet above the contacting elements for discharging cooled effluent gas essentially free of catalyst, and a liquid holdup zone below the inlet for collecting the fuel oil from the contacting elements;
    (c) at least one filter operable in filtration and backwashing modes, wherein the filter comprises a multi-bed system comprising multiple beds, each bed comprising a fixed filtration medium; and
    (d) a filtration loop for circulating fuel oil from the liquid holdup zone through a filter and returning filtrate to the liquid holdup zone.

15. The system of claim 14 further comprising a direct contact inline device that receives and mixes the fluidized-bed propane dehydrogenation reactor effluent and the fuel oil prior to injecting them into a flash zone.

16. The system of claim 14 wherein the fixed filtration medium is a sintered metal filter.

17. The system of claim 14 wherein the filter is a continuous filtration system comprising a drum filter having an inside surface.

* * * * *